United States Patent [19]

Leveskis

[11] 4,154,768

[45] May 15, 1979

[54] PRODUCTION OF HYDROPEROXIDES FROM OLEFINS

[75] Inventor: Newton G. Leveskis, Walnut Creek, Calif.

[73] Assignee: Argus Chemical Corporation, Brooklyn, N.Y.

[21] Appl. No.: 391,692

[22] Filed: Aug. 27, 1973

Related U.S. Application Data

[63] Continuation of Ser. No. 107,536, Jan. 18, 1971, abandoned, which is a continuation-in-part of Ser. No. 663,338, Aug. 25, 1967, abandoned.

[51] Int. Cl.² .......................................... C07C 179/02
[52] U.S. Cl. .................................................. 568/568
[58] Field of Search ........................ 260/610 R, 610 A

[56] References Cited

U.S. PATENT DOCUMENTS

| 2,223,807 | 12/1940 | Milas | 260/610 R |
|---|---|---|---|
| 3,308,163 | 3/1967 | McKellin | 260/610 R |

FOREIGN PATENT DOCUMENTS

191549 1/1967 U.S.S.R. ............................. 260/610 R

OTHER PUBLICATIONS

McCutcheon, "Synthetic Detergents", (1950), p. 273.
Davis et al., "Nature", (1952), vol. 170, No. 4329, p. 668.
Davis et al., "J. Chem. Soc., London", (1953), pp. 1541–1547.

Primary Examiner—James O. Thomas, Jr.
Assistant Examiner—W. B. Lone
Attorney, Agent, or Firm—Townsend and Townsend

[57] ABSTRACT

Increase in yields of alkyl hydroperoxides from corresponding olefins by reacting the olefin with an inorganic peroxide in the presence of an acid catalyst, the acid concentration being adjusted to an optimum range which is generally about 15–30% by total weight of the reactive ingredients. Where the olefin contains over 7 carbon atoms, peroxide-compatible surfactants are included in the reaction mixture and the yield of hydroperoxide is further improved.

6 Claims, 3 Drawing Figures

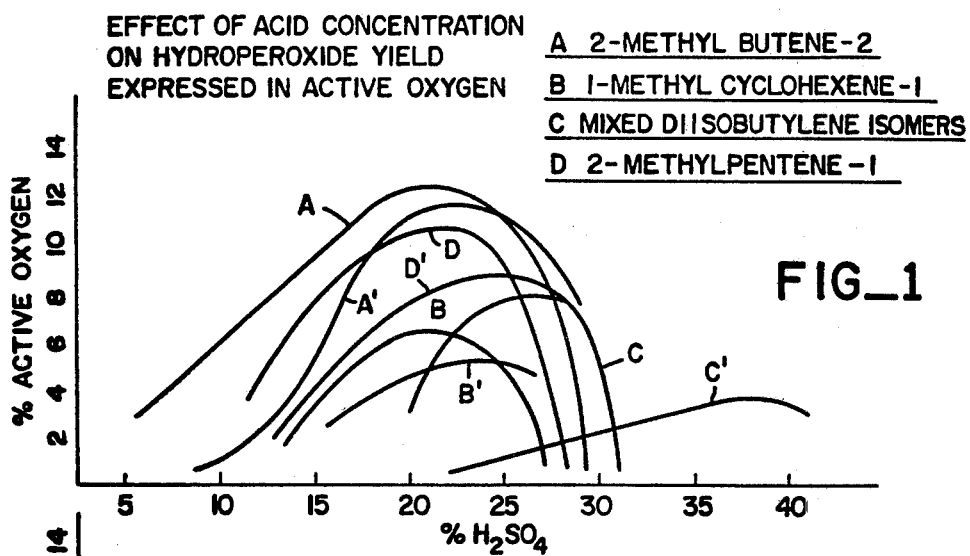
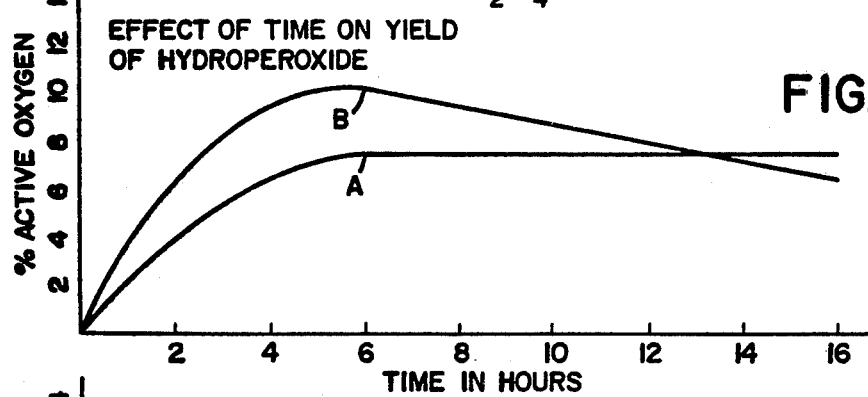
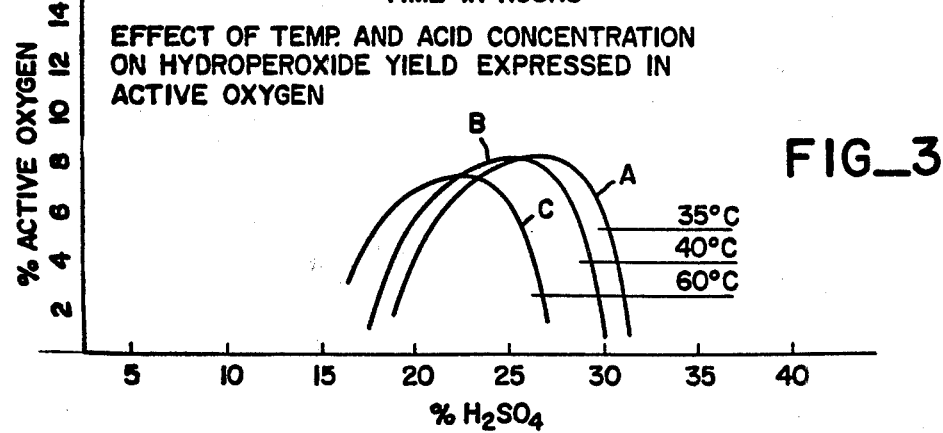

PRODUCTION OF HYDROPEROXIDES FROM OLEFINS

This is a continuation of application Ser. No. 107,536, filed Jan. 18, 1971, abandoned, which is a continuation-in-part of application Ser. No. 663,338, filed Aug. 25, 1967, now abandoned.

This invention relates to the preparation of organic peroxides. More particularly, it relates to the preparation of alkyl hydroperoxides directly from olefins.

The preparation of alkyl hydroperoxides from olefins has been reported by a number of researchers in this art. The earlier literature teaches that hydroperoxides can be prepared by reacting an olefin with an inorganic peroxide such as hydrogen peroxide utilizing a concentrated sulfuric acid catalyst. The acid was employed in trace or minimal amounts generally constituting less than about 1% by weight of the reaction mixture. The reported yields of hydroperoxides obtained were disappointingly low. Subsequently, hydroperoxides were prepared by this reaction in which sulfuric acid was used in relatively high concentrations such as equimolar proportions with respect to the olefin and hydrogen peroxide reactants. Again the yields of desired hydroperoxide products were relatively low. In view of the known tendency of sulfuric acid to react with hydroperoxides and destroy them, the fact that reduced yields were obtained with high acid concentrations is not unexpected.

The present invention is based on the discovery that if the acid concentration in the reaction mixture is adjusted to an optimum point between the two extremes that have heretofore been used, a significant increase in yield of the desired hydroperoxide product can be obtained. Further it has been found that yields can be improved even more if a peroxide-compatible surfactant is added to the reaction mixture. In this regard the addition of such a surfactant to alkenes containing more than 7 carbon atoms results in a dramatic increase in yield of hydroperoxide product.

In the accompanying drawings:

FIG. 1 shows the effect of varying acid concentration and addition of surfactants on yield of several hydroperoxide products.

FIG. 2 illustrates the effect of reaction time on yield of hydroperoxide product prepared by the present improved process.

FIG. 3 illustrates the effect of varying the reaction temperature at which the present improved method is executed.

In more detail, in practicing the improvements of the present invention, the same main reactants are employed that previously have been used. Thus suitable alkene or olefin starting reactants are preferably of an asymmetric secondary character of at least 4 carbon atoms with the double bond associated with the secondary carbon atom so that the resulting hydroperoxide reaction will be of a tertiary character in accordance with the following equation:

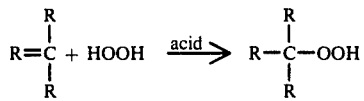

In general, any alkene may be selected although for practical purposes the alkene will contain not more than about 30 carbon atoms.

As before the reaction is generally executed in an aqueous reaction media to which the alkene and the selected inorganic peroxide, preferably hydrogen peroxide, are added in suitable proportions. In general, a slight stoichiometric excess of the inorganic peroxide is desirable to drive the reaction in the direction of hydroperoxide formation.

Any strong acid capable of catalyzing the reaction is contemplated including strong organic acids such as alkylsulfonic acids like methylsulfonic acid. Other preferred acids include strong inorganic acids such as perchloric acid, polyphosphoric acid and phosphoric acid. Best results have so far been obtained with sulfuric acid.

As noted, the inclusion of a surfactant in the reaction media is optional and, if used, will increase the yield of hydroperoxide even beyond that achieved by employing the optimum acid catalyst concentration in connection with the broader aspect of this invention. Where the olefin contains more than 7 carbon atoms, the addition of the surfactant causes a dramatic increase in the yield. Any surfactant that is compatible, i.e. does not react with the inorganic or organic peroxides present in the reaction media, is contemplated. For example, surfactants containing amine groups will generally be avoided since they are usually not stable in an oxidative media.

Typical materials which may be advantageously employed as surfactants include anionic sulfonate type surfactants such as the material known as BENAX 2A1 available from The Dow Chemical Company. A preferred group of surfactants are anionic complex organic phosphate esters such as those available from General Anililine & Film Corporation, Dyestuff & Chemical Division, under the trademark GAFAC. Excellent results have been obtained with GAFAC RE-610. Good results have also been obtained with a nonionic surfactant of General Aniline & Film Corporation, IGEPAL CO-610. Other typical useful ionic surfactants include the alkyl arylsulfonate known commercially as Solar 90 as well as other sulfonates such as sodium xylene sulfonate and sodium benzene sulfonate.

The amount of surfactant employed is variable, depending on the reactants and conditions. In general, a relatively small quantity will result in improved yields. The surfactant usually will not constitute over about 0.5% by weight of the reaction mixture and frequently not over about 0.1% of the reaction mixture.

As noted, the critical factor in achieving the improved yields is in the selection of the optimum acid catalyst concentration. In most cases this acid concentration will be about 5-45% by total weight of the reactive ingredients, with best results being obtained with an acid concentration of about 10-30% by total weight of the reactive ingredients, i.e., the total weight of olefin, acid and peroxide, exclusive of water or impurities.

In FIG. 1 the advantages of the use of an acid concentration in accordance with the present discovery is illustrated in connection with the preparation of four different hydroperoxides. Curves A, B, C, and D were derived respectively from the preparation of tertiary hydroperoxides from 2 methyl butene-2
1 methyl cyclohexene-1
mixed diisobutylene isomers
2-methyl pentene-1

Curves A, B, C, and D were derived from reactions which included the presence of General Aniline & Film Corporation surfactant GAFAC RE-610. Curves A', B', C', and D' were derived from analogous reactions except that the surfactant was omitted. Specifically, the curves were obtained from the reaction of:

1 mole alkene
1.1 mole hydrogen peroxide
3.6 moles water
sulfuric acid to make reaction concentration shown on abscissa.

The total reaction time was 3 hours at a temperature of 35° C. The reactions executed to obtain data for curves A, B, C, and D included 0.1% by weight of the surfactant. Results are shown in terms of percent active oxygen content found in the reaction product mixture.

From FIG. 1 the improvement in yield to be obtained by optimizing the acid catalyst concentration in the preferred range of 5-45% by total weight of reactive ingredients and most preferably 15-30% by total weight of reactive ingredients can be seen. The added improvement in yield resulting from the addition of the surfactant is also illustrated. Attention is directed to curves C and C' which employed a starting alkene reactant mixture in which the molecules each contain 8 carbon atoms. Under these circumstances the addition of the surfactant dramatically improves the product yield. This is typical of the results obtainable where the starting alkenes have more than 7 carbon atoms.

The reaction time needed for substantial product formation is significantly reduced from that which has been previously described in prior processes. In FIG. 2 hydroperoxide was formed from the reaction of 46 gms. of 2-ethyl butene, 37.5 gms. of 50% hydrogen peroxide, and 30 gms. of 65% sulfuric acid. The reaction was run at 35° C. and the yield in terms of percent active oxygen is shown in curve A. Curve B illustrates the same reaction, but with the inclusion of 0.1 gm. of BENAX 2A1 anionic surfactant. It can be seen from the results that substantial yields are obtained rapidly within the first 2 hours with an optimum being reached within 3-6 hours.

The amount of acid catalyst required for optimum yield is affected by the reaction temperature. It has been found that a reaction temperature of 25°-70° C. will permit the use of acid concentrations within the ranges previously indicated for optimum yields. In general, as temperatures are increased, the amounts of acid catalyst required is reduced. However, where the temperature exceeds 70° C. by any appreciable amount, the yield will be reduced even when the acid concentration is reduced. Best results to date have been obtained with reaction temperatures within the range of 30°-50° C.

Curves A, B and C of FIG. 3 were obtained from reactions executed at 35, 40 and 60° C., respectively and illustrate the foregoing temperature considerations. The reaction employed the following materials:

1 mole mixed diisobutylene isomers
1.4 moles hydrogen peroxide
3.6 moles water
sufficient sudfuric acid catalyst to constitute the percent, by total weight of reactive ingredients, indicated along the abscissa.

Although the foregoing invention has been described in some detail by way of illustration and example of purposes of clarity of understanding, it is understood that certain changes and modifications may be practiced within the spirit of the invention as limited only by the scope of the appended claims.

What is claimed is:

1. In a process for converting an asymmetric secondary olefin to a t.-alkyl hydroperoxide by reaction with hydrogen peroxide in a reaction mixture containing a strong acid catalyst selected from the group consisting of sulfuric, phosphoric, alkylsulfonic, polyphosphoric and perchloric acid, the improvement comprising employing said acid catalyst in an amount of about 5-45 percent based on the total weight of reactive ingredients, while maintaining the ingredients at a temperature of about 25°-70° C.

2. The improved process of claim 1 wherein said acid catalyst is added in an amount of about 15-30 percent based on the total weight of reactive ingredients.

3. The improved process in accordance with claim 1 wherein said olefin contains at least eight carbon atoms and said process includes the step of adding up to 0.5 percent by weight of a peroxide-compatible surfactant to the reaction mixture to substantially increase the yield of hydroperoxide as compared with the yield thereof in the absence of surfactant.

4. The improved process in accordance with claim 3 wherein said surfactant is an anionic surfactant.

5. The improved process in accordance with claim 3 wherein said surfactant is a complex phosphate ester.

6. The improved process of claim 1 wherein the acid catalyst is sulfuric acid.

* * * * *